US009443063B2

(12) United States Patent
Ghassemzadeh et al.

(10) Patent No.: US 9,443,063 B2
(45) Date of Patent: Sep. 13, 2016

(54) METHOD AND APPARATUS FOR USING GAIT ANALYSIS TO DETERMINE A HEALTH QUALITY MEASURE

(71) Applicants: AT&T Intellectual Property I, L.P., Atlanta, GA (US); President and Fellows of Harvard College, Cambridge, MA (US)

(72) Inventors: Saeed S. Ghassemzadeh, Andover, NJ (US); Lusheng Ji, Randolph, NJ (US); Robert Raymond Miller, II, Convent Station, NJ (US); Manish Gupta, Cambridge, MA (US); Vahid Tarokh, Cambridge, MA (US)

(73) Assignees: President and Fellows of Harvard College, Cambridge, MA (US); AT&T Intellectual Property I, L.P., Atlanta, GA (US)

( * ) Notice: Subject to any disclaimer, the term of this patent is extended or adjusted under 35 U.S.C. 154(b) by 249 days.

(21) Appl. No.: 14/099,539

(22) Filed: Dec. 6, 2013

(65) Prior Publication Data

US 2015/0161511 A1 Jun. 11, 2015

(51) Int. Cl.
*G06N 99/00* (2010.01)
*G06F 19/00* (2011.01)

(52) U.S. Cl.
CPC ......... *G06F 19/3481* (2013.01); *G06N 99/005* (2013.01); *G06F 19/3431* (2013.01)

(58) Field of Classification Search
None
See application file for complete search history.

(56) References Cited

U.S. PATENT DOCUMENTS 6,632,158 B1 * 10/2003 Nashner ............... A61B 5/1036 434/247
8,099,258 B2 1/2012 Alten et al.
8,206,325 B1 * 6/2012 Najafi ................... A61B 5/1116 600/587
2007/0173903 A1 * 7/2007 Goren ..................... A61N 1/32 607/49
2007/0255186 A1 * 11/2007 Grill ........................ A61H 3/00 600/595
2007/0263907 A1 * 11/2007 McMakin ............ G01S 13/887 382/115
2008/0146968 A1 6/2008 Hanawaka et al.
2008/0214360 A1 * 9/2008 Stirling ................ A61B 5/1038 482/9
2009/0137933 A1 5/2009 Lieberman et al.
2010/0100013 A1 * 4/2010 Hu ........................... A61H 3/00 600/595
2011/0054359 A1 3/2011 Sazonov et al.
2011/0092860 A1 * 4/2011 Salarian ............... A61B 5/4023 600/595
2011/0288379 A1 11/2011 Wu (Continued)

FOREIGN PATENT DOCUMENTS

TW 201315400 A 4/2013

OTHER PUBLICATIONS

Butte, N.F. et al. (Jan. 2012). "Assessing Physical Activity Using Wearable Monitors: Measures of Physical Activity." Medicine & Science in Sports & Exercise vol. 44(1S) Supplement 1, p. S5-S12. DOI: 10.1249/MSS.0b013e3182399c0e.*

(Continued)

*Primary Examiner* — Stanley K Hill
*Assistant Examiner* — Benjamin Buss

(57) ABSTRACT

A method, computer-readable storage device and apparatus for calculating a health quality measure are disclosed. For example, a method receives characteristics of motion information, wherein the characteristics of motion information is based upon gait information, monitors the characteristics of motion information over a time period to determine a plurality of different modes of motion within the time period, and calculates the health quality measure based upon the plurality of different modes of motion.

20 Claims, 3 Drawing Sheets

200
START 205
RECEIVE REQUIRED ACITVITY PROFILE THAT SPECIFIES A DESIRED HEALTH QUALITY LEVEL 210
RECEIVE GAIT INFORMATION 220
CALCULATE CHARACTERISTICS OF MOTION INFORMATION 230
RECEIVE CHARACTERISTICS OF MOTION INFORMATION, WHERE CHARACTERISTICS OF MOTION INFORMATION IS BASED UPON GAIT INFORMATION 240
MONITOR THE CHARACTERISTICS OF MOTION INFORMATION OVER A TIME PERIOD TO DETERMINE A PLURALITY OF DIFFERENT MODES OF MOTION WITHIN THE TIME PERIOD 250
CALCULATE A HEALTH QUALITY MEASURE BASED UPON THE DIFFERENT MODES OF MOTION THAT ARE DETERMINED 260
COMPARE HEALTH QUALITY MEASURE TO HEALTH QUALITY LEVEL SPECIFIED IN REQUIRED ACTIVITY PROFILE 270
TRANSMIT NOTIFICATION INDICATING WHETHER HEALTH QUALITY LEVEL HAS BEEN SATISFIED 280
END 295

(56) References Cited

U.S. PATENT DOCUMENTS

| | | | | |
|---|---|---|---|---|
| 2012/0253234 | A1* | 10/2012 | Yang | A61B 5/1038 600/595 |
| 2012/0253486 | A1 | 10/2012 | Niemimaki | |
| 2013/0006152 | A1 | 1/2013 | Lee et al. | |
| 2013/0103416 | A1 | 4/2013 | Amigo et al. | |
| 2013/0190903 | A1 | 7/2013 | Balakrishnan et al. | |
| 2013/0211290 | A1 | 8/2013 | Lee | |
| 2013/0238287 | A1 | 9/2013 | Hoffman et al. | |
| 2013/0253334 | A1* | 9/2013 | Al-Ali | A61B 5/002 600/476 |
| 2014/0051946 | A1* | 2/2014 | Arne | A61B 5/0022 600/301 |
| 2014/0162933 | A1* | 6/2014 | Hatchwell | C12Q 1/6883 514/1.1 |
| 2014/0257047 | A1* | 9/2014 | Sillay | A61B 5/11 600/301 |
| 2015/0135284 | A1* | 5/2015 | Bogard | G06F 21/31 726/5 |

OTHER PUBLICATIONS

Lara, O.D. et al. (2013). "A survey on human activity recognition using wearable sensors." Communications Surveys & Tutorials, IEEE 15.3: 1192-1209. Date of original publication: Nov. 29, 2012. DOI:10.1109/SURV.2012.110112.00192.*

Li, S. et al. (2011). "A novel gait recognition analysis system based on body sensor networks for patients with parkinson's disease." International Journal of Communication Networks and Distributed Systems 7.3-4: 262-274. DOI:10.1109/GLOCOMW.2010.5700321.*

Avci, A. et al. (2010). "Activity recognition using inertial sensing for healthcare, wellbeing and sports applications: A survey." Architecture of computing systems (ARCS), 2010 23rd international conference on. VDE. 10 pages.*

Sazonov, E.S. et al. (2011). "Monitoring of posture allocations and activities by a shoe-based wearable sensor." Biomedical Engineering, IEEE Transactions on 58.4: 983-990. DOI: 10.1109/TBME.2010.2046738.*

Bernecker, T. et al. (2012). "Activity Recognition on 3D Accelerometer Data (Technical Report)". 22 Pages.*

Schmidt, M. G., "Real-Time Feedback Methods for Gait Rehabilitation Through a Mobile Platform," *Diss. The University of Utah*, 2013.

* cited by examiner

METHOD AND APPARATUS FOR USING GAIT ANALYSIS TO DETERMINE A HEALTH QUALITY MEASURE

BACKGROUND

Pedometers are popular for use as everyday exercise accessories. Often worn on the belt, pedometers can record the number of steps that a user has walked, and thus the distance. Pedometers, or step counters, can provide encouragement to a user to compete with oneself in getting fit and losing weight. However, most pedometers do not have the ability to record and store data. In addition, such pedometers often erroneously record movements other than walking, such as bending to tie shoes, or a road bump while traveling in a vehicle. At the same time, falls are serious hazards for older individuals as coordination, muscle strength, and balance tend to deteriorate with age and advance of chronic diseases such as Parkinson's disease and the like. In managed care as well as home settings, injuries resulting from falls may render older individuals incapable of calling for help and/or requiring emergency treatment. Resulting bone fractures can require lengthy and costly treatment, severely impact quality of life, and can trigger a cascade of other factors that lead to a rapid decline of the health of an individual.

BRIEF DESCRIPTION OF THE DRAWINGS

The present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

In one embodiment, the present disclosure provides a method, computer-readable storage device, and apparatus for calculating a health quality measure. For example, a method receives characteristics of motion information, wherein the characteristics of motion information is based upon gait information, monitors the characteristics of motion information over a time period to determine a plurality of different modes of motion within the time period, and calculates the health quality measure based upon the plurality of different modes of motion.

The present disclosure relates generally to tracking of physical activities and, more particularly, to a method, computer-readable storage device, and apparatus for calculating a health quality measure based upon an analysis of gait information. For example, in one embodiment different modes of human motion are detected through an analysis of a user's gait. The user's gait information is gathered from multiple sensors in the soles of the shoes of the user, collected and sent to a network-based monitoring server to perform gait analysis. In one embodiment, a training data set from a plurality of users is used to create "signatures" for different modes of human motion, or types of activity, e.g., walking, running, jogging, standing, sitting, jumping, cycling, shuffling, falling down, etc. Thus, when analyzing the gait information from a user, characteristics of motion information can be determined from the raw gait information. For example, the characteristics of motion information may include a stride length, a speed, an acceleration, an elevation, and the like. In addition, the characteristics of motion information may also include a mode of motion that is detected based upon the best matching signature. Accordingly, the various modes of motion of the user over time can be monitored and aggregated to calculate a health quality measure for a given time period, such as a number of calories burned, a distance traveled, an activity level, and so forth. A user profile may also be created to store user parameters, such as age and weight, and to track a user's activity level over time. For example, the health quality measure may indicate that the user has been sedentary for an unusual period of time or has a declining activity level compared to a normal activity level for the user, signaling a potential problem or a medical condition.

Figure 1:
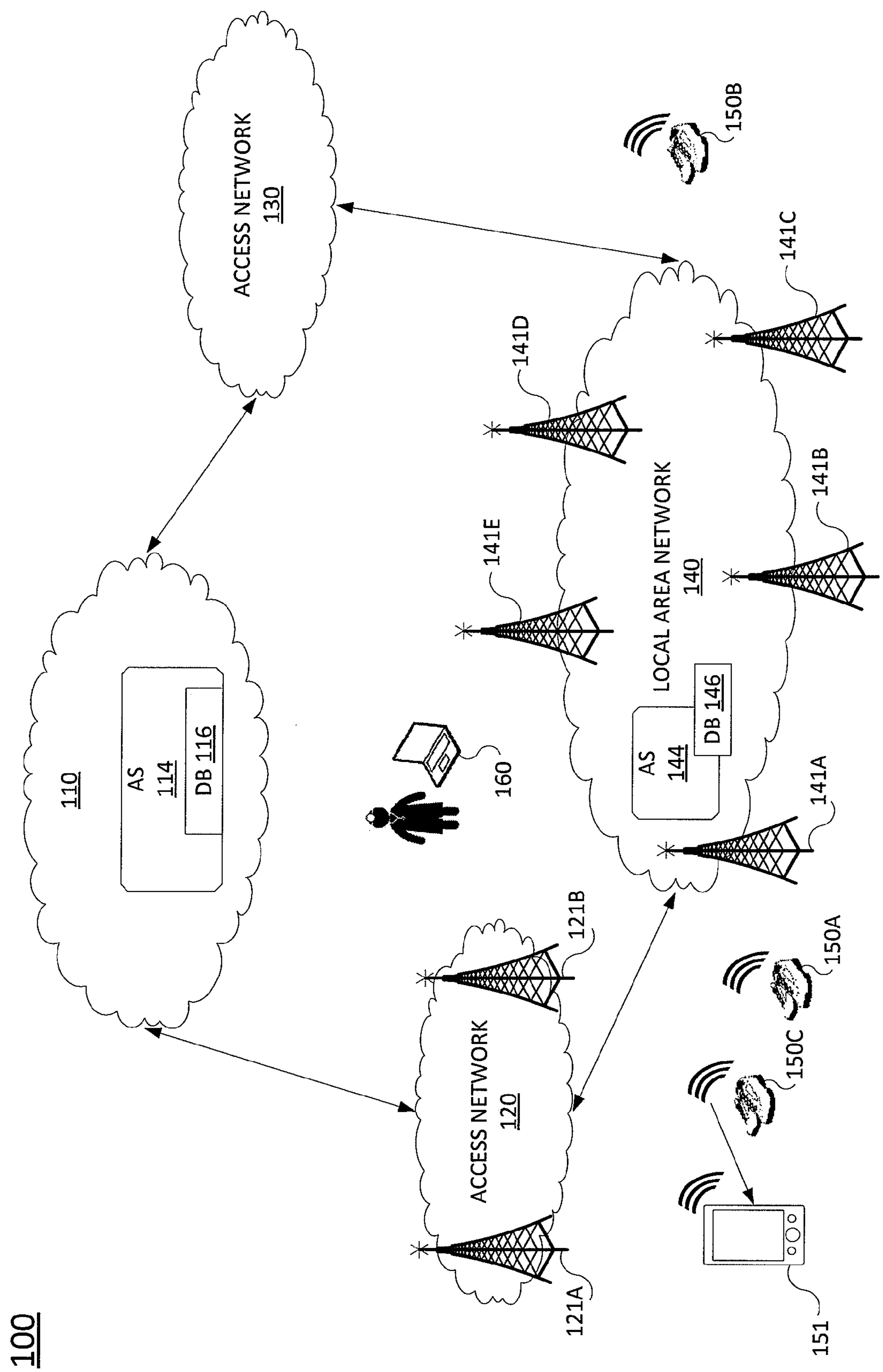
FIG. 1 illustrates one example of a communication network of the present disclosure.

To aid in understanding the present disclosure, FIG. 1 is a block diagram depicting one example of a communication network 100 suitable for use in performing or enabling some or all of the features described herein. The communication network 100 may be any type of communication network, such as for example, a traditional circuit switched network (e.g., a public switched telephone network (PSTN)) or a packet network such as an Internet Protocol (IP) network (e.g., an IP Multimedia Subsystem (IMS) network), an asynchronous transfer mode (ATM) network, a wireless network, a cellular network (e.g., 2G, 3G, and the like), a long term evolution (LTE) network, and the like related to the current disclosure. It should be noted that an IP network is broadly defined as a network that uses Internet Protocol to exchange data packets.

In one embodiment, the network 100 may comprise a core network 110. The core network 110 may be in communication with one or more access networks 120 and 130. For instance, access network 120 may comprise a wireless access network (e.g., an IEEE 802.11/Wi-Fi network, a wide area network (WAN) and the like) or a cellular access network. Thus, in one example, access network 120 may include one or more wireless transceivers 121A and 121B, which may alternatively comprise cellular base stations, base transceiver stations (BTSs), NodeBs, evolved NodeB's (eNodeBs), wireless access points, and so forth. Similarly, access network 130 may comprise a wired access network such as a circuit switched access network, a cable access network, a digital subscriber line (DSL) access network, and so forth. The core network 110 and the access networks 120 and 130 may be operated by different service providers, the same service provider or a combination thereof.

In one embodiment, network 100 also includes a local area network (LAN) 140. For example, local area network 140 may comprise a wireless local area network (LAN), a Bluetooth® network, a ZigBee® network, and so forth. For instance, local area network 140 may be a home network or an office network, e.g., a network that is maintained by a hospital, an elder care facility, a rehabilitation center, and so forth. As illustrated, local area network 140 may comprise a coverage network or mesh network of ZigBee® access points 141A-141E which may be connected to one another and to other devices and networks via an Ethernet network. However, it should be noted that ZigBee® is designed for static end nodes. Thus, local area network 140 may comprise a ZigBee® mesh network modified to enable handoffs between the different ZigBee® access points 141A-141E.

In one example, the ZigBee® access points 141A-141E are in communication with one or more sets of wearable devices 150A-150C. Each of the sets of wearable devices 150A-150C may comprise a pair of "smart" shoes, or shoe inserts. The term "smart" implies ability to measure, record, process, and communicate information. In addition, each of the sets of wearable devices 150A-150C may include one or more components for collecting gait information of a user, such as sole pressure sensors, accelerometers and gyroscopes. The wearable devices may also include notification means, such as an audio alarm, to warn a user of danger (e.g. unstable gait that could result in a proximate fall). In one example, each of the sets of wearable devices 150A-150C comprises a respective component for each foot of a user. However, in another example it may be sufficient to have a single wearable device for only one foot of a user. Notably, the users, and hence the sets of wearable devices 150A-150C, may move throughout the coverage area of local area network 140, thus benefiting from the ability of handing off between the ZigBee® access points 141A-141E.

Figure 3:
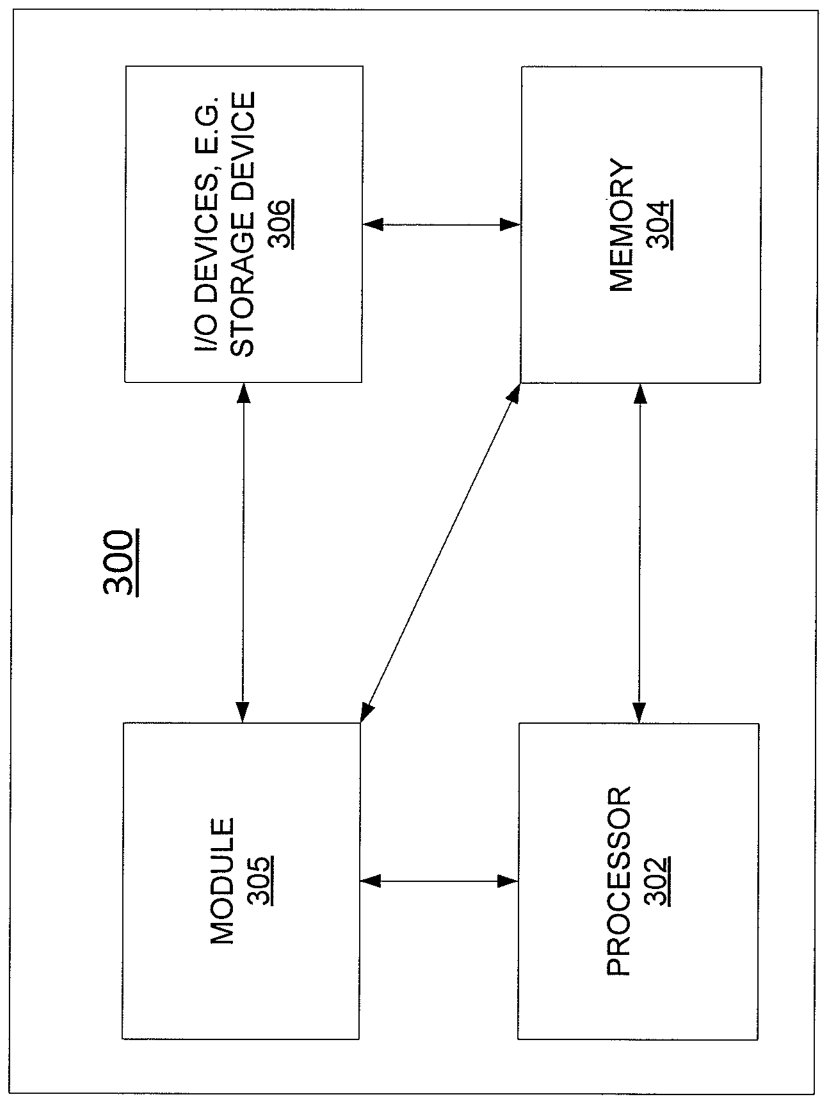
FIG. 3 illustrates a high-level block diagram of a general-purpose computer suitable for use in performing the functions described herein.

In one embodiment, the core network 110 may include an application server (AS) 114 and a database (DB) 116. Notably, AS 114 may perform some or all of the functions described herein in connection with calculating a health quality measure. For example, AS 114 may collect and store in database 116 user gait information received from the one or more sets of wearable devices 150A-150C. Database 116 may also store user profiles, generic signatures for different modes of motion or types of activities and required activity profiles. In one embodiment, gait information may be forwarded from the local area network 140 via access network 120 and/or access network 130 to AS 114. At AS 114, the gait information may be collected, stored in database 116 and used for calculating a health quality measure. In one embodiment, the AS 114 may comprise a general purpose computer as illustrated in FIG. 3 and discussed below. Notably, AS 114 is suitable for performing some or all of the functions of the present disclosure for calculating a health quality measure as described in greater detail below. In addition, although only a single AS 114 and a single DB 116 are illustrated in core network 110, it should be noted that any number of application servers 114 or databases 116 may be deployed.

In one embodiment, the gait information includes information which identifies a particular wearable device or set of wearable devices as a source of the gait information. The gait information may also include pressure information, acceleration information (including both linear and rotational accelerations), gyroscopic information, elevation information, time information and/or location information. In particular, raw gait information, such as pressure information, acceleration information, gyroscopic information, elevation information, temperature and fluid content (edema) may be collected from the various sensors of a wearable device. Other components may also contribute to the gait information prior to the gait information reaching AS 114. For example, each of the ZigBee® access points 141A-141E may time stamp any gait information that is received from one of the sets of wearable devices 150A-150C. In addition, in one example the ZigBee® access points 141A-141E may also append their location information to any gait information that is received. In another example, each ZigBee® access point 141A-141E may simply append its own identity to any gait information that is received, where the identity information is sufficient to indicate the approximate location of the user relative to a corresponding ZigBee® access point, i.e., AS 114 attributes the approximate location of a wearable device 150A-150C to a fixed location of the access point 141A-141E that uploads the gait information.

In one embodiment, AS 114 may also determine characteristics of motion information from the gait information. For example, AS 114 may gather gait information relating to a user over a period of time, e.g., over an hour, over a day, over a week, and so forth. From the gait information, AS 114 may then determine characteristics of motion such as a stride length, a speed, an acceleration, an elevation, and so forth, as well different modes of motion or different types of activities that a user has engaged in at various times within the time period. For example, accelerometers within one of the sets of wearable devices 150A-150C may indicate accelerations along different axes. Accordingly, the raw gait information may simply include an acceleration and an indication of which component recorded the acceleration. Different accelerations may then be vector summed by AS 114 to derive an overall acceleration magnitude and direction which may then be included as part of the characteristics of motion information.

As another example, to determine a mode of motion for any particular time within the time period, AS 114 may compare the gait information/characteristics of motion information to known signatures for different common modes of motion that are stored in database 116. Modes of motion may broadly include postures, stances, movement patterns and/or types of activities, such as: walking, jogging, running, standing, sitting, jumping, cycling, falling and so forth. For instance, a running signature may indicate a sequence of: a strong pressure on the left foot, acceleration of the right foot, a strong force and deceleration of the right foot, acceleration of the left foot, and so forth. On the other hand, a walking signature may be similar to the running signature, but the forces and accelerations observed may be of a lesser magnitude than the signature for running. Similarly, a standing signature may comprise steady and balanced pressure on both feet (with no acceleration). It should also be noted that although several different examples of gait information data sources are describe above, experimental results indicate that success in predicting different modes of motion can be achieved using only pressure data (e.g., without acceleration and/or gyroscopic information).

In one example, training data is generated from test subjects performing known motions, stances and/or postures, e.g., running, jumping, standing, sitting, walking, falling, etc. Each mode of motion can be modeled as a Hidden Markov Model (HMM). For example, a subset of the training data may be used to determine "principal components" associated with different stages of each of the modes of motion, which are the "hidden states" of the HMM. A subset of the training data is also used to determine emission probabilities and transition probabilities between the stages (i.e., between the hidden states). Thus, each HMM may comprise a signature which uniquely identifies one of the different modes of motion. Thereafter, AS 114 may statistically infer a best matching signature/HMM as compared to the observed gait information. In other words, AS 114 assumes the current mode of motion is the one having the HMM that best predicts the currently observed gait information. Illustrative examples of various algorithms for determining different modes of motion, or activity types, can be found in co-pending U.S. patent application Ser. No. 14/099,499, titled "METHOD AND APPARATUS FOR DETECTING MODE OF MOTION WITH PRINCIPAL COMPONENT ANALYSIS AND HIDDEN MARKOV MODEL", filed on the same date herewith which is incorporated by reference herein in its entirety. However, any other methods of determining modes of motion, or activity types can be used by the present method.

Other characteristics of motion, such as speed and stride length, may also be determined from gait information in various ways. For instance, in one embodiment, global positioning system (GPS) location data is included in or appended to the gait information to allow a change in position over time to be determined. In this manner, the average speed and speed at various times may be calculated. In addition, if the mode of motion is determined to be running or walking, the distance traveled in a particular time divided by a number of stances, e.g., steps, observed in the same time will indicate the average stride length. In another embodiment, one or more of the sets of wearable devices 150A-150C may include a pair of sensors, one for each foot, to determine a distance between the sensors. For example, the sensors can send and measure a round-trip time between the sensors, e.g., using infrared signals, radio frequency (RF) signals, acoustic signals, and the like to estimate a distance between the sensors.

In another embodiment, GPS location data may be unavailable. Accordingly, the gait information may include position information derived from one or more other sources. For instance, each of the ZigBee® access points 141A-141E may append its identity and/or location information to any gait information that the ZigBee® access point receives and forwards, thereby allowing AS 114 to determine the approximate location of a user at different times. For example, at a first time, gait information for the set of wearable devices 150A may be received and appended with the identity and/or location of ZigBee® access point 141A. At a later time, gait information may be received for the same set of wearable devices 150A from ZigBee® access point 141B. Thus, AS 114 can determine the approximate distance traveled, speed and so forth, based upon the difference in positions of the respective ZigBee® access points.

Once various characteristics of motion are determined (including a number of different modes of motion the user has engaged in during a given time period), AS 114 may then determine a health quality measure based upon the different modes of motion. For example, the health quality measure may comprise: a number of calories burned, a distance traveled, an average speed, a time spent performing a particular type of activity/mode of motion in the given time period, a score comparing a current level of activity to a previous level of activity, a number of medical episodes during the given time period, and so forth. For example, to determine a number of calories burned, database 116 may contain a lookup table that correlates user parameters, such as age and weight, with characteristics of motion information, such as speed and mode of motion to allow AS 114 to determine the number of calories burned. In other words, the characteristics of motion information may include additional data that may be used in conjunction with information on the mode(s) of motion to calculate the health quality measure. As another example, AS 114 may similarly determine a speed or a distance traveled in a given time period by considering the change in the relevant characteristics of motion information or the average over the time period.

It should be noted that the health quality measure may account for several different modes of motion that the user has engaged in during the relevant time period. For example, the user may wake up and go for a jog for 30 minutes. The user may then spend an hour mainly walking and standing in the user's home getting ready for the day. The user may then spend most of the day primarily sitting in the car and at the user's desk at work. There may be some walking in the office but the characteristics of motion information will mostly show that the user was sitting. Following work, there may be another 30 minutes of sitting as the user drives home. The user may then engage in two hours of sitting and standing as the user straightens up the home, prepares dinner and sits down for a meal. The user may then go for a 30 minute walk after dinner followed by another hour of sitting as the user watches a television program before preparing to sleep. In the foregoing scenario, the user engages in various modes of motion at different times throughout the day. These different modes of motion are determinable by comparing the gait information/characteristics of motion information that is collected to signatures for different modes of motion to detect a best match. Thus, the user's day can be segmented into time periods where the user is engaged in different modes of motion. When aggregated, AS 114 is then able to track the user's entire history of motion throughout the day. In one example, the health quality measure may then be a percentage of time that the user engaged in vigorous exercise, e.g., running, jogging, cycling, etc.

As mentioned above, in one example the health quality measure may comprise a number of medical episodes during a given time period. Thus, in addition to signatures for the common modes of motion, database 116 may store profiles for modes of motion associated with various medical conditions. For instance, "falling" may have a specific signature. Similarly, akinesia (lack of movement) and hypokinesia (reduced amplitude of movement), associated with Parkinson's disease, may have their own unique signatures. Incidents of these conditions may be controlled to some degree with medication or physical therapy. However, if a patient is not responding to medication or fails to take the medication as prescribed, the number of occurrences of these types of incidents may increase. Thus, in one example the health quality measure may comprise the number of incidents of this nature in the given time period. In addition, in one example, the health quality measure may be reported to a monitoring entity such as a doctor, a nurse, a physical therapist, a sports coach, and the like in order to allow the monitoring entity to contact the user to offer encouragement, to discuss with the user any issues which may be affecting the user's condition, and so forth.

In this regard, it should be noted that in one embodiment, AS 114 may further consider the health quality measure in connection with a required activity profile that specifies a target health quality level. For example, a monitoring entity may determine various parameters that they would like the user to satisfy in a particular time period. To illustrate, a physical therapist may direct the user to walk continuously for at least one hour each day and to attempt to make strides that are greater than two feet in length. In another example, a doctor may request that the user not sit for more than 8 hours per day. Accordingly, the health quality measure calculated by AS 114 may indicate whether the user has satisfied the target health quality level specified in the particular required activity profile. In addition, in one embodiment, AS 114 may also send a report to the monitoring entity indicating whether the target health quality level has been satisfied. Thus, the monitoring entity can contact the user to offer encouragement, to discuss any matter which may be helping the user to satisfy the target health quality level or which may be hindering the user from meeting the goal, and so forth.

In one embodiment, the health quality measure may comprise a score that may be compared to past scores for the user or to an average score and/or a target score for an ideal user in the same demographic group. For example, in one embodiment a score of 10 may indicate that the user has satisfied a required activity profile for the day, while a score of 8 may indicate that the user only came close to meeting his or her goal. In another embodiment, a score of 5 may indicate that user is average within a demographic group with respect to a particular health quality measure, e.g., calories burned in one 24 hour period, while a score of 9 may indicate that the user is within the top ten percent of users within the demographic group with respect to the same health quality measure. In still another example, AS 114 may store a user profile that stores health quality measures relating to a user over a period of time. For example, AS 114 may determine that a user has been relatively sedentary for several days, as compared to a normal or average level of activity for the user, based upon the health quality measures taken over the entire week. This may signal a potential problem or a medical condition. Thus, the user, a medical provider and/or a caregiver may be alerted to further investigate.

The foregoing describes various functions of AS 114 (and database 116) in connection with embodiments of the present disclosure for calculating a health quality measure. However, it should be noted that in one example, local area network 140 may also include an application server (AS) 144 and a database 146 which may perform the same or similar functions to those of AS 114 in core network 110. In other words, AS 144 may also collect and store user gait information from the one or more sets of wearable devices 150A-150C via the ZigBee® access points 141A-141E. Database 146 may also store user profiles, instructions relating to the tracking of different users, mode of motion signatures, required activity profiles, and so forth to allow AS 144 to determine characteristics of motion information and/or to calculate a health quality measure locally. In one embodiment local area network 140 also provides access for endpoint device 160, e.g., a personal computer, a laptop computer, tablet computer, smart phone, and the like to connect to AS 144 and/or AS 114. For example, a doctor, a nurse, a technician, a patient, and so forth may use endpoint device 160 to access AS 114 and/or AS 144. In one embodiment, endpoint device 160 is connected directly to local area network 140. However, in another embodiment, endpoint device may be a remote device that connects to local area network 140 and AS 144 via one or more of access network 120, access network 130 and or core network 110.

In one example, one or more of the sets of wearable devices, e.g., set 150C, may also communicate with a cellular base station 121A and/or 121B of access network 120 to upload gait information to a server performing functions for calculating a health quality measure. For example, the set of wearable devices 150C may include a subscriber identity module (SIM) card, a cellular antenna and/or any other components that may be required to enable cellular communications via access network 120. Alternatively, or in addition, the set of wearable devices 150C may communicate with access network 120 via cellular device 151. For example, cellular device 151 may comprise an intermediary unit, such as a cell phone, a personal base station, a femtocell or the like, for providing a tethering function to the set of wearable devices 150C. In other words, the set of wearable device 150C and the cellular device 151 may communicate using various cellular communication standards or using near field communication techniques such as Wi-Fi/IEEE 802.11, Bluetooth®, ZigBee® and so forth. Regardless of the specific technology or communication techniques used, access network 120 may thus receive gait information from the set of wearable devices 150C and forward such information to a server performing functions for calculating a health quality measure of the present disclosure.

In one example, the gait information is uploaded to AS 114 in the core network 110. However, in another example, the gait information may be passed to AS 144 in the local area network 140. For example, in one embodiment gait information of a user may still be managed via AS 144 in the local area network 140 when the user is not currently proximate to the local area network 140 and/or is not within range to communicate directly with components of local network 140.

In one embodiment, local area network 140 may comprise an indoor network, e.g., a combination of wired and wireless LANs within a user's home or of a medical facility such as a hospital, a rehabilitation center, an elder care facility, and the like. Thus, local area network 140 and access network 120 may be complimentary to one another, with local area network 140 providing the capability of uploading gait information while a user is indoors, and with the access network 120, e.g., a cellular network, providing coverage while the user is outdoors and/or while the user is outside of the communication range of the local area network 140.

In one embodiment, each of the sets of wearable devices 150A-150C may be configured to connect to local area network 140 and the ZigBee® access points 141A-141E when available, and to connect to access network 120 only when the local area network 140 is not available. In one example, when connecting to access network 120, the cellular device 151 may time stamp the gait information as well as append to or include location information with the gait information that the cellular device receives and uploads to a network-based server, e.g., AS 114. For example, if the gait information is passed from the set of wearable devices 150C via a cellular phone to access network 120, the cellular phone may indicate the GPS location information of the phone. Thus, the GPS location information of the phone can be associated with the contemporaneous gait information of the set of wearable devices 150C. As an alternative, or in addition, each of the base stations 121A and 121B may calculate location information of the device from which the base station receives the gait information based upon cell tower triangulation, distance and direction estimation and so forth. Thus, when AS 114 and/or AS 114 receives gait information, regardless of whether it is received from local area network 140 or from access network 120, the gait information may include location information and/or time information, in addition to the other parameters such as acceleration, pressure, and so forth obtained by the sensors of a set of wearable devices.

It should be noted that the network 100 has been simplified. For example, the network 100 may include other network elements (not shown) such as border elements, routers, switches, policy servers, security devices, gateways, administrator and user consoles, and so forth.

Figure 2:
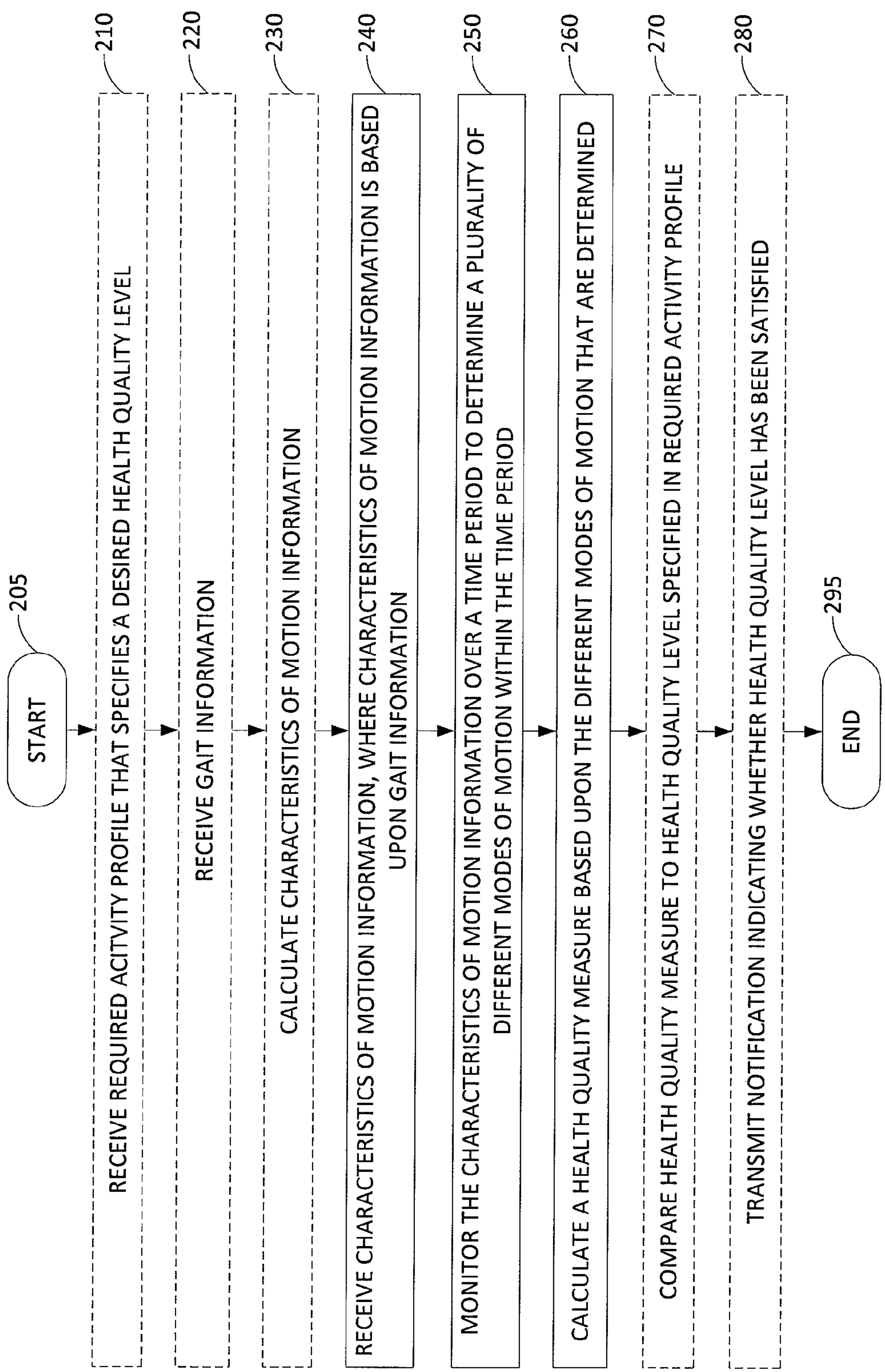
FIG. 2 illustrates an example flowchart of a method for calculating a health quality measure, according to the present disclosure.

FIG. 2 illustrates an example flowchart of one embodiment of a method 200 for calculating a health quality measure, according to the present disclosure. In one embodiment, the method 200 may be performed by an application server such as AS 114 or AS 144 as illustrated in FIG. 1. In one embodiment, the steps, functions, or operations of method 200 may be performed by a computing device or system 300, and/or processor 302 as described in connection with FIG. 3 below. For illustrative purpose, the method 200 is described in greater detail below in connection with an embodiment performed by a processor, such as processor 302.

The method 200 begins at step 205 and proceeds to optional step 210. At step 210, the processor may receive a required activity profile that specifies a target health quality level. For example, a monitoring entity such as a doctor, a nurse, a physical therapist, a sports coach, etc., may determine various parameters that they would like a user, or patient, to satisfy in a particular time period. For example, a doctor may request that the user not sit for more than 8 hours per day. Similarly, a physical therapist may direct the user to walk continuously for at least one hour each day and to attempt to make strides that are greater than two feet in length.

At optional step 220, the processor receives gait information of a user. For example, a set of wearable devices may collect gait information from a number of sensors such as linear accelerometers, gyroscopes, pressure sensors and the like. The processor may receive the gait information from the set of wearable devices via one or more intermediary networks such as a local area network, e.g., a local area network (LAN) that may comprise a ZigBee® mesh network, a wired and/or a wireless/cellular access network, and so forth. In one example, the set of wearable devices and/or one or more intermediary components may also append a time stamp and/or location information to the gait information before the gait information is received by the processor.

At optional step 230, the processor calculates characteristics of motion information from the gait information that may be received at step 220. For example, at the previous optional step 220 the processor may receive gait information continuously and/or periodically over a period of time. From the temporal sequence of the gait information, the processor may then determine such motion parameters as a stride length, a speed, an acceleration, an elevation, and so forth, as well different modes of motion or different types of activities that a user is engaged in at various times within the time period. For example, to determine one or more modes of motion that may be indicated by the gait information, the processor may compare the gait information to known signatures for different common modes of motion/types of activities.

At step 240, the processor receives characteristics of motion information that is based upon gait information. For instance, the processor may itself determine the characteristics of motion information, e.g., when performing optional steps 220-230. However, in another embodiment the processor may simply receive the characteristics of motion information from another device. For example, the processor may be a processor of a centralized application server, whereas the functions/operations of steps 220-230 may be performed by another device prior to forwarding the characteristics of motion information to the centralized application server.

At step 250, the processor monitors the characteristics of motion information over a time period to determine a plurality of different modes of motion within the time period. For example, the activities of a user may be monitored over the course of several hours, over a day, over a week, over a month and so forth. Consequently, a typical user will likely engage in various different types of activities within the time period such as walking, jogging, running, standing, sitting, jumping, cycling, falling and so forth. In one embodiment, at step 250 the processor determines the different modes of motion that are exhibited as well as the times/durations demonstrated for each of the different modes of motion. For instance, step 250 may involve determining that the user was cycling for one hour, standing for 30 minutes and sitting for 4.5 hours in a six hour period.

At step 260, the processor calculates a heath quality measure based upon the different modes of motion that are determined. For example, a health quality measure may comprise one or more of: a distance traveled, an average speed, a number of medical episodes during the given time period, and so forth. For example, at previous step 250 the user's day can be segmented into time periods where the user is engaged in different modes of motion. When aggregated, the processor is then able to track the user's entire history of motion throughout the day. Thus, in one example, the health quality measure may be a percentage of time that the user engaged in vigorous exercise, e.g., running, jogging, cycling, etc. In addition, in a further example, the heath quality measure may comprise a number of calories burned. Notably, the processor may calculate an overall number of calories burned in a given time period by taking into account the different modes of motion observed during the time period, the duration for which the user engaged in each of the different modes of motion, as well as user parameters such as the user's age, weight, height, gender, metabolic rate and so forth. In addition, the processor may further account for the pace in which the user engages in certain activities, e.g., a speed when running. Thus, the user's exertions over different activities/modes of motion during the time period can be aggregated to come up with an overall health quality measure, e.g., a number of calories burned.

Following step 260, the method may proceed to optional step 270, where the processor may compare the health quality measure to a health quality level specified in a required activity profile. For example, the processor may have previously received the required activity profile at optional step 210. Accordingly, at step 270 the processor may compare the health quality measure calculated at step 260 with the target health quality level specified in the required activity profile. For instance, a physical therapist may direct the user to walk continuously for at least one hour each day and to attempt to make strides that are greater than two feet in length. Thus, the health quality measure may indicate whether or not the user has achieved this goal.

At optional step 280, the processor may transmit a notification of whether the health quality level has been satisfied. In other words, depending upon the determination at step 270, the processor may notify the user, a medical provider, a caregiver, a sports coach, etc. In one example, the notification is sent only if the health quality level is not met. However, in another example, the notification is also sent when the health quality measure indicates that the health quality level has been satisfied. For example, it may be desirable to notify the user or a monitoring entity to provide encouragement or to simply have a complete picture of the user's activities from day to day, week to week, etc.

Following any one or more of steps 260, 270 or 280, the method 200 proceeds to step 295 where the method ends.

It should be noted that although not explicitly specified, one or more steps, operations or blocks of the method 200 described above may include a storing, displaying and/or outputting step as required for a particular application. In other words, any data, records, fields, and/or intermediate results discussed in the methods can be stored, displayed, and/or outputted to another device as required for a particular application. Furthermore, steps, operations or blocks in FIG. 2 that recite a determining operation, or involve a decision, do not necessarily require that both branches of the determining operation be practiced. In other words, one of the branches of the determining operation can be deemed as an optional step. Furthermore, operations, steps or blocks of the above described methods can be combined, separated, and/or performed in a different order from that described above, without departing from the example embodiments of the present disclosure.

FIG. 3 depicts a high-level block diagram of a general-purpose computer suitable for use in performing the functions described herein. As depicted in FIG. 3, the system 300 comprises a hardware processor element 302 (e.g., a central processing unit (CPU), a microprocessor, or a multi-core processor), a memory 304, e.g., random access memory (RAM) and/or read only memory (ROM), a disk drive, an optical drive, a magnetic drive, and/or a Universal Serial Bus (USB) drive, a module 305 for calculating a health quality measure, and various input/output devices 306 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Furthermore, although only one general-purpose computer is shown in the figure, if the method(s) as discussed above is implemented in a distributed manner for a particular illustrative example, i.e., the steps of the above method(s) or the entire method(s) are implemented across multiple general-purpose computers, then the general-purpose computer of this figure is intended to represent each of those multiple general-purpose computers.

It should be noted that the present disclosure can be implemented in software and/or in a combination of software and hardware, e.g., using application specific integrated circuits (ASIC), a general purpose computer or any other hardware equivalents, e.g., computer readable instructions pertaining to the method(s) discussed above can be used to configure a hardware processor to perform the steps, functions and/or operations of the above disclosed methods. In one embodiment, instructions and data for the present module or process 305 for calculating a health quality measure (e.g., a software program comprising computer-executable instructions) can be loaded into memory 304 and executed by processor 302 to implement the steps, functions or operations as discussed above in connection with the exemplary method 200. The processor executing the computer readable or software instructions relating to the above described method(s) can be perceived as a programmed processor or a specialized processor. As such, the present module 305 for calculating a health quality measure (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. More specifically, the computer-readable storage device may comprise any physical devices that provide the ability to store information such as data and/or instructions to be accessed by a processor or a computing device such as a computer or an application server. In addition, it should be noted that the hardware processor can be configured or programmed to cause other devices to perform one or more operations as discussed above. In other words, the hardware processor may serve the function of a central controller directing other devices to perform the one or more operations as discussed above.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A method for calculating a health quality measure, the method comprising:

receiving, by a processor deployed in a communication network, characteristics of motion information, wherein the characteristics of motion information is based upon gait information;

monitoring, by the processor, the characteristics of motion information over a time period to determine a plurality of different modes of motion within the time period, wherein the plurality of different modes of motion comprises: running, walking, falling, jumping, standing, cycling and sitting; and calculating, by the processor, the health quality measure based upon the plurality of different modes of motion, wherein the health quality measure comprises a number of medical episodes during the time period.

2. The method of claim 1, wherein the gait information comprises pressure information, acceleration information, and gyroscopic information.

3. The method of claim 1, wherein the plurality of different modes of motion is included in the characteristics of motion information.

4. The method of claim 3, wherein the characteristics of motion information further comprises at least one of: a stride length, a speed, an acceleration, and an elevation.

5. The method of claim 1, wherein the health quality measure further comprises at least one of: a number of calories burned, a time spent performing a particular type of activity during the time period, a distance traveled, an average speed, or a score comparing a current level of activity to a previous level of activity.

6. The method of claim 1, further comprising:

receiving an activity profile that specifies a target health quality level.

7. The method of claim 6, further comprising:

comparing the health quality measure to the target health quality level specified in the activity profile; and transmitting a notification indicating whether the target health quality level has been satisfied.

8. The method of claim 6, wherein the activity profile is determined by a medical provider.

9. The method of claim 1, further comprising:

receiving the gait information from a set of wearable devices.

10. The method of claim 1, wherein the characteristics of motion information is determined based upon the gait information by comparing the gait information that is received to a plurality of signatures of mode of motion.

11. The method of claim 10, wherein each of the plurality of signatures of mode of motion comprises a hidden markov model.

12. The method of claim 1, wherein the gait information is received via one of: a cellular access network and a ZigBee mesh network.

13. The method of claim 12, wherein a set of wearable devices is for gathering the gait information and for communicating the gait information to one of: the cellular access network and the ZigBee mesh network.

14. The method of claim 13, wherein the set of wearable devices communicates the gait information to the ZigBee mesh network when the set of wearable devices is within a communication range of the ZigBee mesh network and wherein the set of wearable devices communicates the gait information to the cellular access network when the set of wearable devices is not within a communication range of the ZigBee mesh network.

15. The method of claim 13, wherein the set of wearable devices communicates the gait information to the cellular access network via an intermediary cellular endpoint device.

16. The method of claim 1, wherein the gait information is time stamped prior to the gait information being received by the processor.

17. A computer-readable storage device storing instructions which, when executed by a processor deployed in a communication network, cause the processor to perform operations for calculating a health quality measure, the operations comprising:

receiving characteristics of motion information, wherein the characteristics of motion information is based upon gait information;

monitoring the characteristics of motion information over a time period to determine a plurality of different modes of motion within the time period, wherein the plurality of different modes of motion comprises: running, walking, falling, lumping, standing, cycling and sitting; and calculating the health quality measure based upon the plurality of different modes of motion, wherein the health quality measure comprises a number of medical episodes during the time period.

18. An apparatus comprising:

a processor deployed in a communication network; and a computer-readable storage device storing instructions which, when executed by the processor, cause the processor to perform operations, the operations comprising:

receiving characteristics of motion information, wherein the characteristics of motion information is based upon gait information;

monitoring the characteristics of motion information over a time period to determine a plurality of different modes of motion within the time period, wherein the plurality of different modes of motion comprises: running, walking, falling, jumping, standing, cycling and sitting; and calculating a health quality measure based upon the plurality of different modes of motion, wherein the health quality measure comprises a number of medical episodes during the time period.

19. The apparatus of claim 18, wherein the gait information comprises pressure information, acceleration information, and gyroscopic information.

20. The apparatus of claim 18, wherein the plurality of different modes of motion is included in the characteristics of motion information.

* * * * *